US011103671B2

(12) United States Patent
Bogin et al.

(10) Patent No.: US 11,103,671 B2
(45) Date of Patent: Aug. 31, 2021

(54) PORTABLE DEVICES FOR ADMINISTRATION OF THERAPEUTIC GAS MIXTURES AND METHODS OF USE

(71) Applicant: NOBILIS THERAPEUTICS, INC., Portland, CA (US)

(72) Inventors: Vlad Bogin, Portland, OR (US); Larry Williamson, Coronado, CA (US)

(73) Assignee: Nobilis Therapeutics, Inc., Portland, OR (US)

( * ) Notice: Subject to any disclaimer, the term of this patent is extended or adjusted under 35 U.S.C. 154(b) by 519 days.

(21) Appl. No.: 15/861,455

(22) Filed: Jan. 3, 2018

(65) Prior Publication Data

US 2018/0185608 A1 Jul. 5, 2018

Related U.S. Application Data

(60) Provisional application No. 62/441,676, filed on Jan. 3, 2017.

(51) Int. Cl.
*A61M 16/20* (2006.01)
*A61M 16/12* (2006.01)
*A61M 16/00* (2006.01)
A61M 15/00 (2006.01)
A61M 21/02 (2006.01)
A61M 16/04 (2006.01)

(52) U.S. Cl.
CPC ........ *A61M 16/204* (2014.02); *A61M 16/024* (2017.08); *A61M 16/12* (2013.01); *A61M 16/20* (2013.01); *A61M 15/008* (2014.02); *A61M 15/0081* (2014.02); *A61M 16/049* (2014.02); *A61M 16/208* (2013.01); *A61M 21/02* (2013.01); *A61M 2202/025* (2013.01); *A61M 2202/0208* (2013.01); *A61M 2202/0225* (2013.01); *A61M 2202/0258* (2013.01); *A61M 2202/0283* (2013.01); *A61M 2202/0291* (2013.01); *A61M 2205/3553* (2013.01); *A61M 2205/3584* (2013.01); *A61M 2205/3592* (2013.01); *A61M 2205/8225* (2013.01)

(58) Field of Classification Search
CPC .. A61M 16/20; A61M 16/201; A61M 16/202; A61M 16/203; A61M 16/204; A61M 15/0013; A61M 15/016; A61M 15/002; A61M 15/0021; A61M 15/0025; A61M 15/0068; A61M 15/007; A61M 15/0071; A61M 15/0081; A61M 16/18; A61M 16/183
See application file for complete search history.

(56) References Cited

U.S. PATENT DOCUMENTS 2,041,406 A * 5/1936 Foregger ............ A61M 16/104
128/205.12
2,866,456 A * 12/1958 Lovy ........................ A62B 9/02
128/205.24

(Continued)

*Primary Examiner* — Michael J Tsai
(74) *Attorney, Agent, or Firm* — Baumgartner Patent Law; Marc Baumgartner

(57) ABSTRACT

Disclosed herein are portable gas delivery systems and therapeutic methods of use. More specifically, the portable gas delivery systems herein include a regulator having an inhalation device, such as a mouthpiece, and is configured to operably couple with removable sealed gas cartridges that comprise a therapeutic gas mixture of either one or more noble gases or nitrous oxide.

6 Claims, 5 Drawing Sheets

(56) References Cited

U.S. PATENT DOCUMENTS

| | | | | |
|---|---|---|---|---|
| 2,952,526 | A * | 9/1960 | Carlson | A62B 19/00 422/120 |
| 3,326,231 | A * | 6/1967 | Hogg | F17B 1/12 137/318 |
| 3,800,819 | A * | 4/1974 | McKee | A61M 16/00 137/343 |
| 4,370,997 | A * | 2/1983 | Braithwaite | F16K 17/04 137/116.3 |
| 4,694,850 | A * | 9/1987 | Fumino | A61M 16/10 137/318 |
| 4,940,049 | A * | 7/1990 | Kirchgeorg | A61M 16/00 128/204.18 |
| 5,507,277 | A * | 4/1996 | Rubsamen | A61M 15/00 128/200.14 |
| 5,660,172 | A * | 8/1997 | Hatton | A62B 7/02 128/201.28 |
| 6,585,016 | B1 * | 7/2003 | Falligant | A61M 16/183 141/352 |
| 8,684,240 | B2 * | 4/2014 | Sauer | B67D 1/0418 222/396 |
| 2004/0129270 | A1 * | 7/2004 | Fishman | A61M 16/0051 128/204.18 |
| 2006/0124129 | A1 * | 6/2006 | Wharton | A61M 15/0051 128/204.26 |
| 2007/0017520 | A1 * | 1/2007 | Gale | A61M 16/101 128/204.26 |
| 2012/0116292 | A1 * | 5/2012 | Montgomery | A61B 90/94 604/24 |
| 2013/0333704 | A1 * | 12/2013 | Duncan | B63C 11/22 128/205.22 |
| 2014/0053835 | A1 * | 2/2014 | Gilbert | A61M 15/08 128/203.14 |
| 2014/0090644 | A1 * | 4/2014 | Aldana | A61M 16/12 128/203.23 |

* cited by examiner

PORTABLE DEVICES FOR ADMINISTRATION OF THERAPEUTIC GAS MIXTURES AND METHODS OF USE

CROSS-REFERENCE TO RELATED APPLICATIONS

This application claims priority to U.S. Provisional Application No. 62/441,676, filed Jan. 3, 2017, which is incorporated herein by reference in its entirety

FIELD OF THE INVENTION

The invention pertains to the field of portable therapeutic gas administration devices. More particularly, the invention relates to an improved apparatus which is convenient and easy for the patient themselves to operate for use in (stressful, anxiety-induced, etc.) situations outside of clinical settings and/or guidance or supervision of a medical provider.

BACKGROUND

Therapeutic uses of gases, including nitrous oxide and noble gases, have been utilized in some medical facilities and have been documented in preclinical and some pilot clinical settings. While some medical benefits from these gases have been observed, there are also serious dangers and risks known to be associated with the administration of nitrous oxide and noble gas mixtures to patients. As one example, nitrous oxide and noble gases are known to be the types of asphyxiant gases. While nontoxic or minimally toxic, these types of gases can reduce normal oxygen concentration in the lungs of a treated patient. Oxygen depletion can of course, in turn lead to asphyxiation and death in the patient if the administration of the asphyxiant gas is not performed safely. Because of these health risks, in addition to the high cost of xenon, and the complexity of current gas administration devices, all current nitrous oxide and noble gas therapeutic administration is provided in a medical facility (e.g., hospital or clinic) under the supervision of a trained medical professional, often requiring cardiovascular and pulmonary monitoring. Unfortunately, traveling to a medical facility for treatment is costly and time-consuming for the patients. These problems are further exacerbated when the patient to be treated is already suffering from high stress and/or anxiety.

Compact, portable gas delivery devices designed for use in an emergency are known in the art. For example, U.S. Pat. No. 2,428,425 and U.S. Pat. No. 4,996,982 (Williamson) disclose portable breathing apparatuses designed to be used in emergencies, such as for situations where breathable air is unavailable. This can include underwater dives when the main tank runs out of air, fires, or a drop in oxygen levels in an aircraft during depressurization. As these prior devices were designed for emergency air intake to prevent suffocation of the user, they did not contemplate or were otherwise configured to be used with medical administration of nitrous oxide or a noble gas, which are well-known asphyxiants. It is important to note that due to their very different objectives from the present invention, these prior art devices did not include instructions from a medical provider for guiding a patient on how to inhale, non-exclusively including directions for breath type, such as length and strength of inhalation, and the number of inhalations needed to achieve the desired medical effect. Prior art users of these emergency breathing devices would just breathe as needed during the dangerous situation. Furthermore, these prior art emergency breathing devices did not include any form of child protective locks to prevent inadvertent use by children, which is at least advisable to incorporate, if not required by law.

Accordingly, there is a need in the art to provide an easy-to-use, safe and effective portable device which allows for the safe administration of nitrous oxide or noble gas to a patient in need, such as though suffering from anxiety and/or depression. These devices preferably include instructions from a medical provider directing how the patient should breathe during use, and include a locking device to prevent undesired use from someone other than the patient, such as a child.

SUMMARY

Various aspects of the invention are enumerated in the following paragraphs:

The invention embodies devices and methods of providing a small, quantity of a therapeutic gas mixture to be self-administered by patients in a non-clinical setting. The device is sufficiently safe and effective to meet the standards of the FDA (in the USA) and [other regulatory bodies in ex-US territories] for home use. According to preferred embodiments, the device is compact (e.g., can be entirely held and operated in one hand of the using patient), rugged, durable and portable, as well as simple and safe for the user to operate, especially in stressful environments, especially without the need for a medical provider being present to administer.

Preferred methods herein comprise: administering a compressed noble gas or nitrous oxide gas mixture to a patient in need comprising: identifying a patient in need of the gas mixture, such that they are suffering from a condition selected from the group consisting of: neurological disorders, anxiety depression, pain relief, inflammation, and stress disorders, providing a portable, handheld, gas delivery system, said gas delivery system comprising: a sealed pressurized cartridge containing a predetermined amount of compressed therapeutic gas mixture comprising either nitrous oxide or a noble gas mixture; a demand regulator comprising: (a) a cartridge receiver configured to releasably couple with the pressurized cartridge in a sealed connection with the regulator and allow intake of the gas mixture into the regulator based on the inhalation type of the patient; (b) an inhalation device; and (c) an outtake, where said demand regulator components are configured such that the inhalation of the patient through the inhalation device actuates the release of a portion of the gas mixture from the pressurized cartridge through the cartridge receiver into the regulator while lowering the pressure of the gas mixture within the regulator to ambient pressure, or substantially so, and then allows the gas mixture to enter into the patient's lungs from the regulator through the inhalation device; and further allows the patient's exhalation through the inhalation device to be released from the regulator through the outtake; and instructions from a medical provider to the patient directing a breath type during use; and the patient inhaling an amount the gas mixture through the inhalation device in accordance with the breath type provided in the instructions in an amount sufficient to alleviate said condition.

Preferred devices herein comprise a portable, handheld, gas delivery system, said gas delivery comprising: i) a sealed pressurized cartridge containing a predetermined amount of compressed therapeutic gas mixture comprising either nitrous oxide or a noble gas mixture; ii) a demand regulator comprising: (a) a cartridge receiver configured to releasably couple with the pressurized cartridge in a sealed connection with the regulator and allow intake of the gas mixture into the regulator based on the inhalation type of the patient; (b) an inhalation device; and (c) an outtake, where said demand regulator components are configured such that the inhalation of the patient through the inhalation device actuates the release of a portion of the gas mixture from the pressurized cartridge through the cartridge receiver into the regulator while lowering the pressure of the gas mixture within the regulator to ambient pressure, or substantially so, and then allows the gas mixture to enter into the patient's lungs from the regulator through the inhalation device; and further allows the patient's exhalation through the inhalation device to be released from the regulator through the outtake; and iii)instructions from a medical provider to the patient directing a breath type during use.

DETAILED DESCRIPTION OF THE INVENTION

Figure 1:
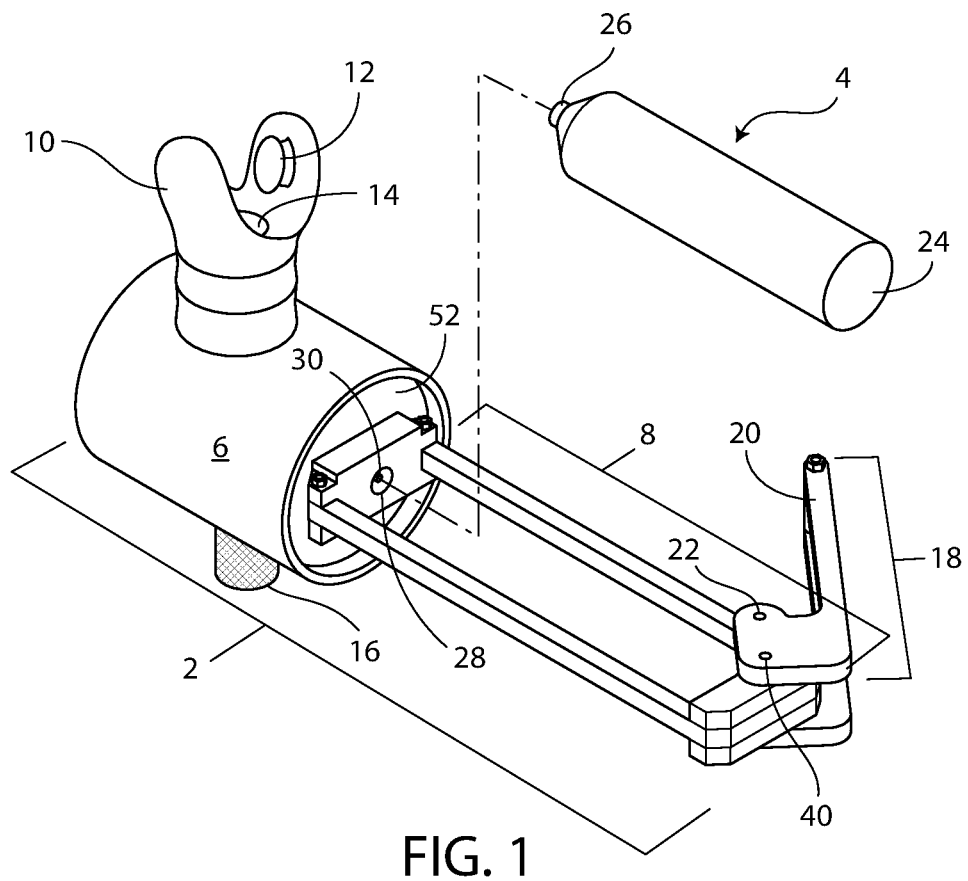
FIG. 1 is a perspective view of a gas delivery system, with the cartridge removed.

The present invention provides a portable apparatus for delivery of therapeutic gases and mixtures thereof which is compact (e.g., can be held with a single hand and operated with a single hand or even without hands such as just being held by the user's mouth), sealed, rugged and virtually maintenance free.

According to preferred embodiments, the gas delivery systems 2 provided herein include two main parts: i) a regulator 6 and ii) a cartridge receiver 8, configured to securely receive a detachable pressurized gas cartridge 4 in a sealed connection that allows gas flow into the regulator 6 from the cartridge 4.

Regulator

The regulator 6 preferably includes an intake such as a regulator stem 30 operably coupled to the detachable gas cartridge 4 to allow for gas 38 to enter from the cartridge 4 into the regulator 6. According to preferred embodiments, the regulator components are configured such that the inhalation of the patient through the mouthpiece 10 activates the regulator 6 to release a portion of the noble gas or nitrous oxide mixture from the pressurized cartridge 4 through the intake/cartridge receiver 28 and lower the pressure of the gas mixture 38 within the regulator 6 to ambient pressure, or substantially so, and allows the gas mixture 38 to enter into the patient's mouth and lungs from the regulator 6 through the mouthpiece 10; and further allows the patient's exhalation through the mouthpiece 10 to be released from the regulator 6 through one or more outlets/outtakes (e.g., exhaust valve(s)) 42.

While any suitable regulator can be used with the teachings herein, according to preferred embodiments, the regulator 6 is a demand valve that delivers gas 38 only while the user is inhaling and reduces the gas pressure from the pressurized cartridge 4 to ambient pressure, or substantially so. According to preferred embodiments, the demand regulator is coupled to the pressurized detachable gas cartridge 4 that contains a predetermined amount (based on a medical provider's recommended dosage and safety guidelines) of a specified mixture of medical gases, including noble gas mixtures or nitrous oxide. The regulator 6 includes a mouthpiece 10 that fits within the user's mouth to allow gas 38 from the regulator 6 to enter their lungs and their circulation.

Demand regulators 6 are known in the art and as the name implies, supply the user only the gas flow rate and volume that is needed at each moment, no more or less. When the user stops inhaling, the flow of gas stops. In general, a demand regulator has a regulator valve for regulating the flow of the gas mixture from the cartridge 4 to a user through a supply valve, controlling the supply of the gas mixture from within the cartridge to the regulator valve. Without being bound to a particular mechanism, demand regulators typically have a sensing diaphram that moves downwards when suction is applied (through inhalation), this movement in turn can be readily configured to move contacting levers to open air flow. According to preferred embodiments, a pliable exhaust ring 52 is positioned on the underside of the regulator 6 and covers the outlets/outtakes 42 to prevent exhaled gases from escaping in its natural position. As the user exhales into the mouthpiece, the exhaust disc bends away from the outlets/outtakes 42 and allows the exhaled breath to escape from the regulator 6.

The regulator 6 can be similar to any suitable breathing regulator non-exclusively including auxiliary breathing devices such as the demand regulators sold by SPARE AIR™, including models 300, 300-N and 170, for example. Thus, there is no learning curve or skill needed to use the device. Given that users of the device are expected to be people who may be suffering from a variety of ailments such as stress, anxiety, depression, including PTSD, Panic attacks, and Alzheimer's, or have recently suffered a brain trauma, it is preferred that the breathing experience with the delivery system 2 be as simple as possible. Thus, according to preferred embodiments, the devices herein don't have extraneous parts that don't further the objectives provided herein.

Cartridge

The cartridge 4 is configured to hold a predetermined therapeutic gas mixture 38 (prescribed by a medical provider) and sealed under pressure. The volume and pressure of the gas 38 in the cartridge 4 will be set to deliver any suitable number of doses in a safe manner. Preferably this will be between 4-20 or 4-30 breaths of the gas 38 until the gas in the cartridge 4 is fully depleted. Preferred cartridges have a capacity of about 5-20 L of gas mixture, and more preferably 10 L. Preferred cartridges 4 are filled with compressed gas at between 400 psi and 2500 psi operating pressure. According to preferred embodiments, the cartridge 4 is made of metal, but can be made of any suitable materials.

Figure 4:
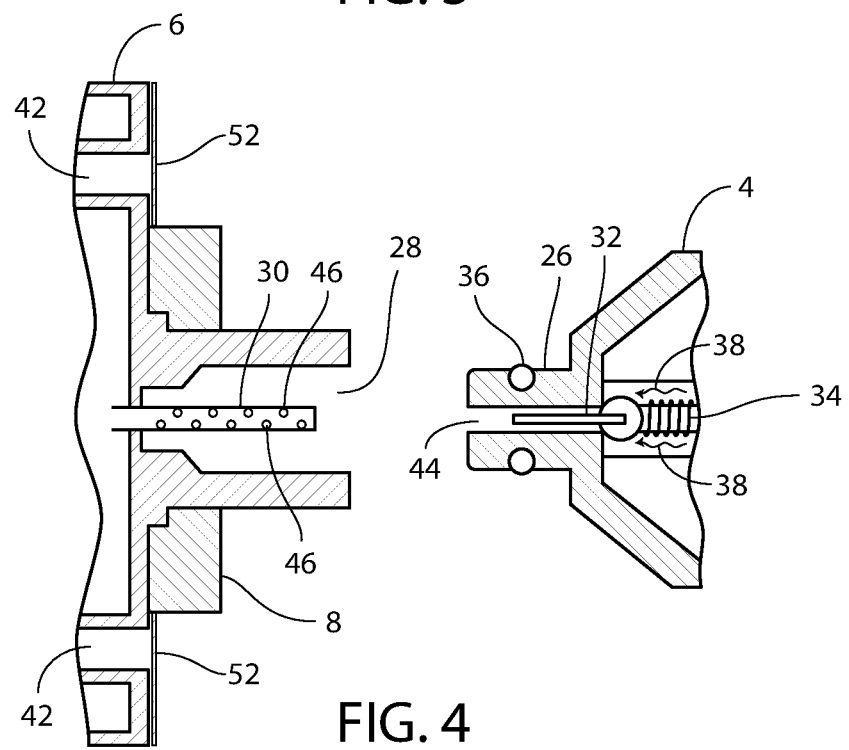
FIG. 4 is an internal view of a detached cartridge and cartridge receiver on the regulator.
Figure 5:
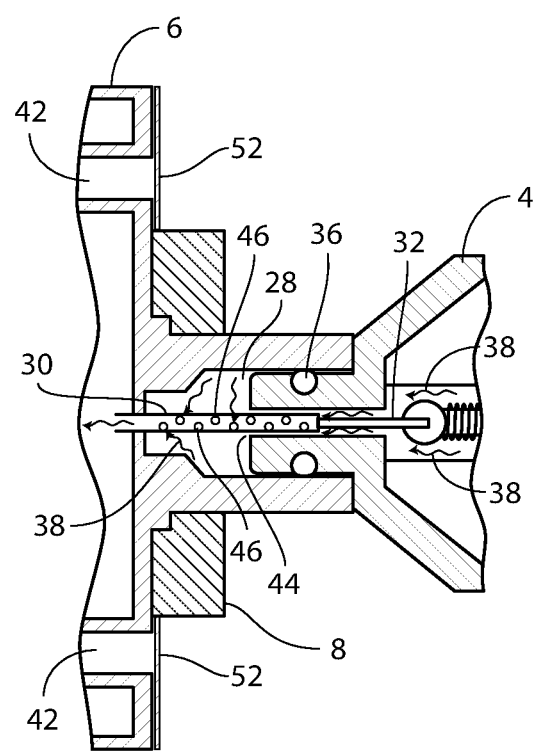
FIG. 5 is an internal view of the cartridge coupling with the cartridge receiver on the regulator.
Figure 6:
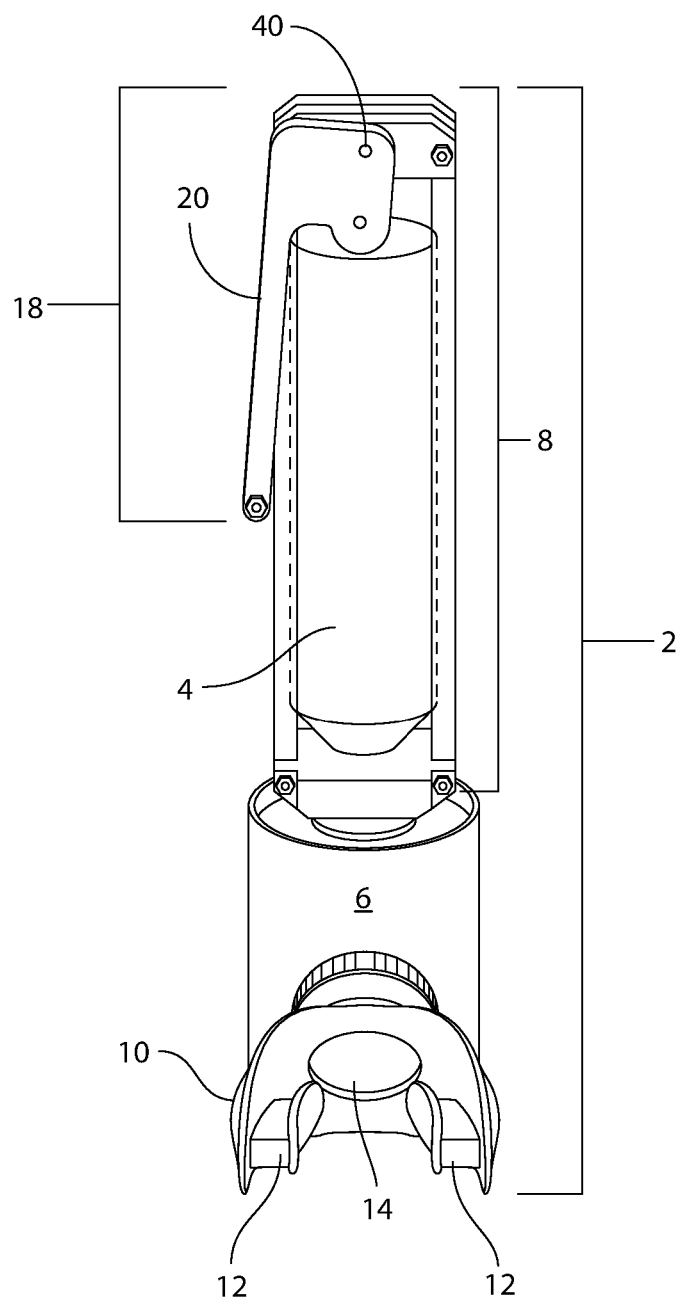
FIG. 6 is a front perspective view of a gas delivery system with the quick release device in a closed position.
Figure 7:
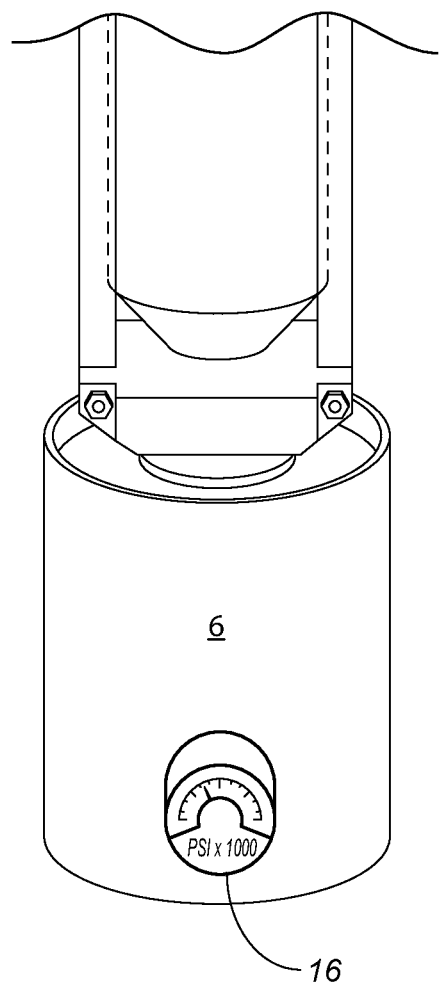
FIG. 7 is a back perspective view of a gas delivery system with the quick release device in a closed position.

According to preferred embodiments, the cartridge 4 includes a proximal section (e.g., nipple 26) configured to operably couple with the cartridge receiver 28 (on the regulator 6) and a distal end 24. FIGS. 4 and 5 show a preferred internal view of the components of the cartridge 4 that interact with the cartridge receiver 28. This embodiment includes a nipple 26 having an external O-ring 36 that is configured to fit within the cartridge receiver 28 and allow gas flow from the cartridge 4 out of a channel 44 and into the intake(s) 46 and into the regulator 6. One, non-exclusive way of doing this is to utilize a check valve 32/spring 34 within the channel 44 of the cartridge 4. The cartridge 4 and the cartridge receiver 28 are detached in FIG. 4. This view shows the check valve 32 in its natural position, without compression of the coupled spring 34. In this natural configuration, no significant amount of gas 38 can escape the cartridge 4.

In FIG. 5 the cartridge 4 is engaged with the cartridge receiver 28. As shown, the nipple 26 is inserted into the cartridge receiver 28 and the O-ring 36 fits snugly within the internal walls of the cartridge receiver 28 to create a gas seal. Thus, the internal diameter of the cartridge receiver 28 is larger than the section of the cartridge configured to be inserted (e.g., the nipple 26). As the nipple 26 is inserted into the cartridge receiver 28, the regulator stem 30 engages with the check valve 32, pushing it away towards the distal end 24 of the cartridge, and compressing the coupled spring 34. This action opens the channel 44 to allow gas 38 flow out of the cartridge 4. The gas 38 can then travel through one or more intake holes 46 within the regulator stem 30 to enter the regulator. Other regulator stems are also envisioned with the teachings herein, such as tapered, solid (without holes), or triangular shaped stems that allow gas to travel around it and into the regulator 6.

According to further embodiments, other types of gas cartridges can be used with the teachings herein. For example, common detachable $CO_2$ cartridges without valves, such as cartridges designed to quickly fill bike tube or for use with air guns, can be used, but are not preferred as they can leak and make it harder to control the amount of gas to be administered. These cartridges often lack internal valves and just have a puncturable seal that allows the gas to be released after puncture. These pressurized cartridges often require turning a standard screw thread against the bottom of the cartridge to lock and unlock the cartridge. SODASTREAM® sells devices that allow users to carbonate water and other flavored drinks to create sparking water drinks and sodas. SODASTREAM® $CO_2$ canisters have an internal check valve within and have external coarse threads called Acme threads that allow a user to screw the cartridge into their respective receivers. The above described processes are cumbersome and if it is not carried out with some level of skill, the device could easily deliver the wrong dose, due to leakage, or no dose at all. The cartridges 4 shown in FIGS. 4-5 are a vast improvement in function ability, reliability and user friendliness than prior art $CO_2$ canisters. These improvements are significant as they allow the devices to deliver a successful therapy to a stressed or mentally impaired user.

The exact number of turns needed to unscrew and replace prior art $CO_2$ canisters can be difficult for a given user to ascertain. Users of prior art $CO_2$ canisters have reported that they are not sure if they have turned the cylinder enough times or not.

Cage

Figure 2:
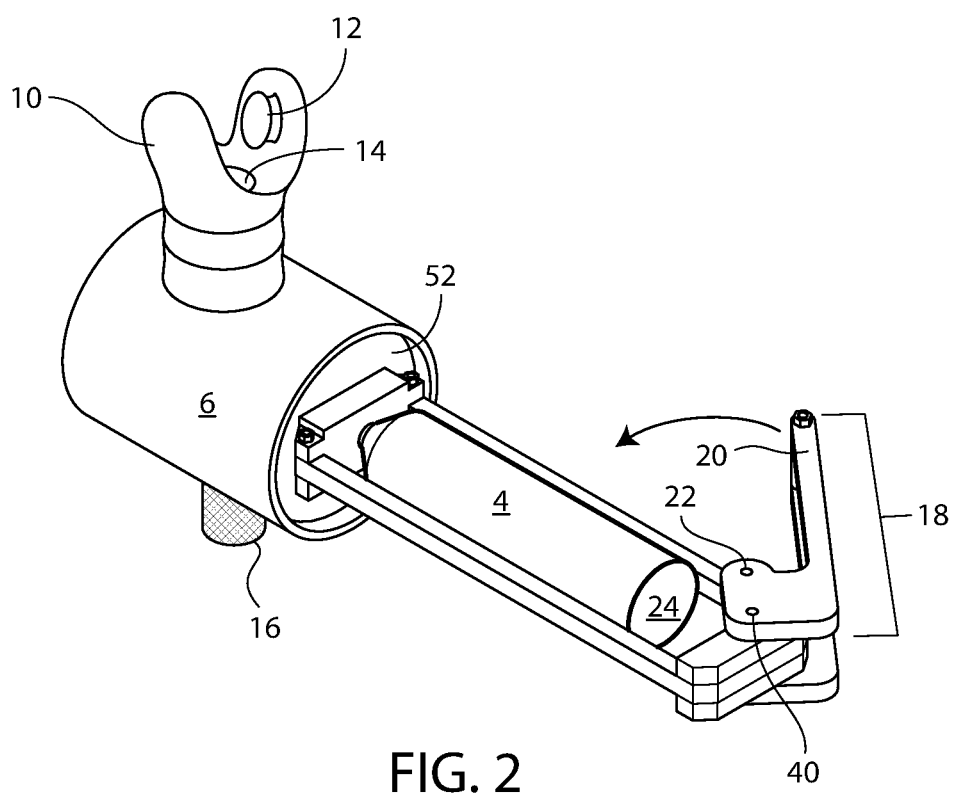
FIG. 2 is a perspective view of a gas delivery system with the quick release device in an open position.
Figure 3:
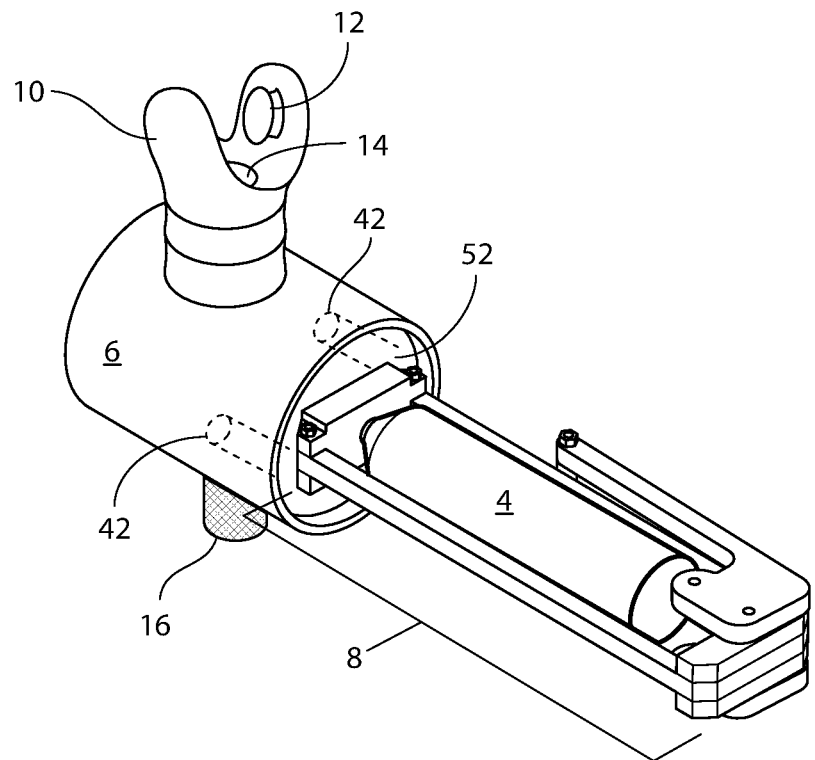
FIG. 3 is a perspective view of a gas delivery system with the quick release device in a closed position.

The cage 8 holds the detachable cartridge 4 in such a way as to allow a secure and sealed coupling with the cartridge receiver 28, while at the same time being very quick and easy to change. The cage 8 has multiple functions for the devices described herein. Firstly, it can be configured to be easily held by the user, before, prior or during use. Additionally, the cage 8 can protect the cartridge 4 from drops or other accidents. Furthermore, the cage 8 has one or more openings configured to allow a new cartridge or old cartridge to pass through. Still further, the cage 8 can act as a scaffolding or support for a quick release 18 that can securely hold the cartridge 4 into the cartridge receiver 28. According to this embodiment, the quick release 18 includes a cam 22 and lever 20 operably to the cage 8 at a pivot point 40 that allows the cam 22 and lever 20 to swivel into open (FIGS. 1 and 2) and closed positions (FIG. 3). In the open configuration as shown in FIGS. 1 and 2, the quick release 18 the lever 20 and cam 22 are positioned away from the cage 8. This position allows an old cartridge 4 to either be removed from the regulator 6 or a new cartridge to be inserted into the cartridge receiver 28. Once the cartridge 4 is placed into the cartridge receiver 28, the quick release 18 can be closed by moving the lever 20 towards the cage 8. This actuates the cam 22 to swivel towards the cartridge 4, specifically engaging with the underside distal end 24 of the cartridge 4 and applying pressure into the cartridge receiver 28. It is preferred that when the lever 20 is pressed against the cage 8, the top most portion of the coupled cam 22 presses against and is aligned along the same vertical axis as the cartridge's distal end 24 to lock it into place. This tight pressure between the cam 22 and the distal end 24 of the cartridge 4 (the cartridge 4 is pushing distally in to the cam 22) holds the lever 20 in its locked positioned against the cage 8. A user observing the lever 20 reach its end of range motion against the cage 22 can verify that the cartridge 4 is indeed securely locked in place. Using minimal force, the user can pull the lever 20 away from the cage 8 thereby swiveling the cam 22 at the pivot point 40 away from the distal end 24 of the cartridge 4 and allowing it to be removed from the cartridge receiver 28.

The above quick release device 18 is superior to $CO_2$ cartridges described above, such as the $CO_2$ cartridges used for air guns and SODASTREAM®, as these devices must overcome added resistance that pushes the cartridge away from their respective intakes. Failure to provide an upward force in these types of cartridges can at best result in decreased efficiency and at worst to failure due to impaired gas flow or gas leaking and becoming depleted over a short period due to lack of an effective seal. The teachings herein overcome these potential problems by using the simple cam 22 and lever 20 action to apply an upward force to the cartridge 4 proximally and secure it there.

Other release mechanisms can be used herein besides those shown in the Figures. As one example a knob that can be tightened to apply upward pressure against the cartridge and can be loosened in the opposite direction to relieve said upward pressure.

Additionally, other shapes and cage configurations are readily envisioned for use with the teachings herein, including fully enclosed cases (with or without holes) that are hinged to allow installation and removal of the cartridge, and sheaths with a lower distal opening allowing the cartridge 4 to be pressed up into the cartridge receiver 28. According to non-preferred embodiments, no cage is utilized with the delivery systems 2 herein, and the cartridge 4 simply couples with the cartridge receiver 28 without protection. These cartridges can be screwed or snapped into the regulator to lock them into place using any suitable mechanism.

Mouthpiece/Inhalation Device

The mouthpiece 10 has a passage 14 that allows the user to inhale from and exhale into the regulator 6, while minimizing dilution of the therapeutic mixture 38 with atmospheric gases. Exhaled gas flows out through the mouthpiece 10 and exits the regulator via one or more outlet(s)/outtake(s) 42 (e.g., exhaust valve) at the bottom portion of the regulator 6. The mouthpiece 10 preferably has a mouth-engaging portion having a passage 10 therethrough, and is either U or V shaped, or similarly so, having two extending portions curved inward toward one another and tapering to a distal end, the extending portions facilitating rapid insertion into a user's mouth. According to preferred embodiments, the mouthpiece 10 is streamlined and tapered which allows for easy insertion into the mouth for quick administration of gas 38 when needed. The mouthpiece 10 is preferably inserted entirely within the patient's mouth to prevent therapeutic gas 38 from leaking out, and assuring that the fully desired dose is administered. The mouthpiece 10 preferably includes one or more bite tabs 12 to help stabilize the delivery system 2 and prevent slippage. The mouthpiece 10 can be made of any suitable material, but is preferably pliable to alleviate discomfort and make use easier. Preferred materials non-exclusively include silicone or pliable plastic, for example. While the term mouthpiece is used predominantly herein, any inhalation device allowing a user to inhale the therapeutic gas (and exhale their outbreath) can be used with the regulator. According to alternative embodiments, a face mask that covers both the user's mouth and nose can be used with the teachings herein as an inhalation device instead of a mouthpiece. Any suitable style of face mask can be used, non-exclusively rigid masks, and pliable masks that help prevent gas from leaking, such as silicone face masks. As some non-exclusive examples, oxygen masks used in hospitals, or for passengers or pilots in airplane emergencies, can be used herein. According to non-preferred embodiments, a nasal cannula or catheter can be used instead of a mouthpiece as an inhalation device.

Safety Guard

Figure 8:
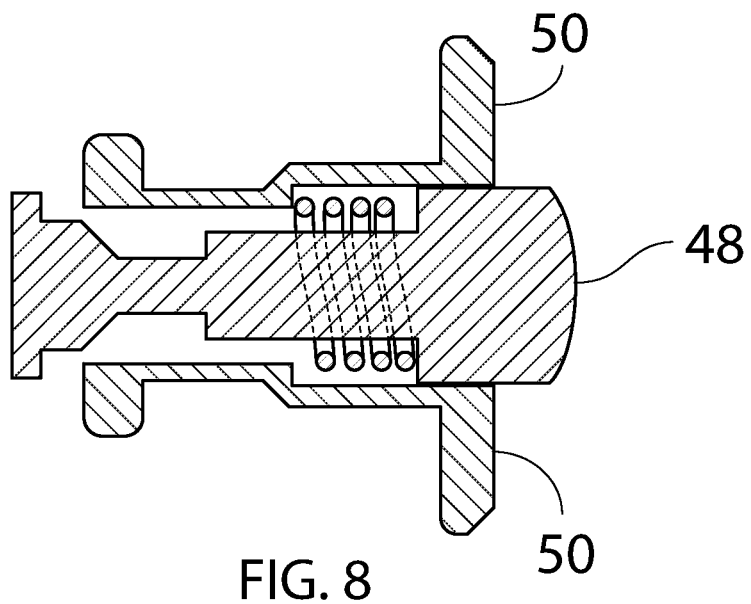
FIG. 8 is an internal view of a removable mouthpiece lock.
Figure 9:
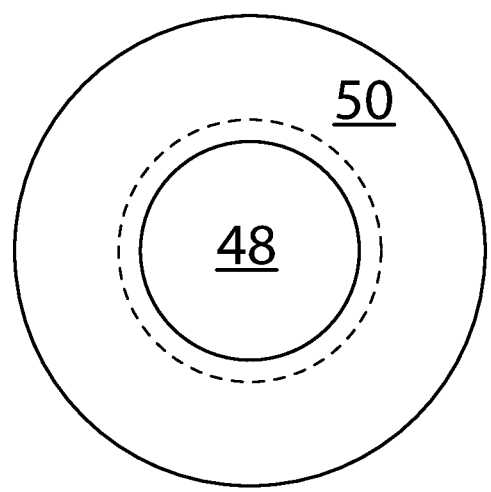
FIG. 9 is a top view of a removable mouthpiece lock.

Additionally, a removable mouthpiece cover 52 can be incorporated that functions either as a child-proof lock and/or protection of the breathing chamber of the regulator from accumulating undesirable foreign objects such as oil, dust, or the like. For example, the mouthpiece cover can use tabs, pull pins, and/or child-proof threads to prevent undesired use. Another example, as shown in FIGS. 8 and 9, is a dual release guard 52 that can be used to lock and unlock the mouthpiece 10 to prevent and allow use, respectively. For example, the mouthpiece guard 52 can be configured with a plunger 44 and a pull ring 46, such that the user must depress the plunger 44 and simultaneously lift on the pull ring 46 to remove the guard 52 and access the mouthpiece 10. Any suitable lock can be used with the teachings herein. Additional locking mechanisms can include a storage or travel case that is locked and must be unlocked to access the delivery system.

Gas Mixtures

A variety of therapeutic gas mixtures can be utilized with the teachings herein. According to preferred embodiments, the gas mixtures utilized herein are either 1) a mixture of one or more noble gases or 2) a nitrous oxide mixture.

Noble Gas Mixtures

Noble gas mixtures can include one or more of the following noble gases: Xenon, Argon, Krypton, Helium, Neon with a remaining non-active portion including a mix of oxygen and nitrogen. Preferred embodiments are directed to a noble gas mixture within the cartridge of one of the following four mixtures: 1) Xenon, Oxygen, and Nitrogen, 2) Xenon, Argon, Oxygen, and Nitrogen, 3) Argon, Oxygen, and Nitrogen, and 4) Xenon, Argon, and Oxygen. If only one noble gas is used in the mixture, it is preferred that sole noble gas makes up between 10-55%, and more preferably between 18-30% of the total gas volume in the cartridge. It is likewise preferred that the remainder of the volume is made up of a mixture of nitrogen and oxygen. In other embodiments when 2 or more noble gases are used, it is preferred that the two or more noble gases make up between 30-70% of the total gas volume in the cartridge. It is likewise preferred that the remainder of the volume is made up of oxygen or of a mixture of nitrogen and oxygen. Xenon and Argon either used as the sole noble gas or together are the more preferred noble gases to be used with the teachings herein.

The following Xenon gas mixture embodiments can be used with the teachings herein. In further embodiments, Argon and Helium can readily be substituted for Xenon in these mixture ratios.

55% by volume xenon/25% by volume oxygen/20% by volume nitrogen;
55% by volume xenon/30% by volume oxygen/15% by volume nitrogen;
55% by volume xenon/35% by volume oxygen/10% by volume nitrogen;
55% by volume xenon/40% by volume oxygen/5% by volume nitrogen;
55% by volume xenon/45% by volume oxygen;
50% by volume xenon/50% by volume oxygen;
50% by volume xenon/45% by volume oxygen/5% by volume nitrogen;
50% by volume xenon/40% by volume oxygen/10% by volume nitrogen;
50% by volume xenon/30% by volume oxygen/20% by volume nitrogen;
50% by volume xenon/25% by volume oxygen/25% by volume nitrogen;
45% by volume xenon/55% by volume oxygen;
45% by volume xenon/50% by volume oxygen/5% by volume nitrogen;
45% by volume xenon/45% by volume oxygen/10% by volume nitrogen;
45% by volume xenon/40% by volume oxygen/15% by volume nitrogen;
45% by volume xenon/35% by volume oxygen/20% by volume nitrogen;
45% by volume xenon/30% by volume oxygen/25% by volume nitrogen;
45% by volume xenon/30% by volume oxygen/25% by volume nitrogen;
40% by volume xenon/30% by volume oxygen/30% by volume nitrogen;
40% by volume xenon/50% by volume oxygen/10% by volume nitrogen;
35% by volume xenon/25% by volume oxygen/40% by volume nitrogen;

35% by volume xenon/65% by volume oxygen;
30% by volume xenon/70% by volume oxygen;
30% by volume xenon/50% by volume oxygen/20% by volume nitrogen;
30% by volume xenon/30% by volume oxygen/40% by volume nitrogen;
20% by volume xenon/80% by volume oxygen;
20% by volume xenon/30% by volume oxygen/50% by volume nitrogen;
15% by volume xenon/30% by volume oxygen/55% by volume nitrogen;
15% by volume xenon/50% by volume oxygen/35% by volume nitrogen;
10% by volume xenon/90% by volume oxygen;
10% by volume xenon/50% by volume oxygen/40% by volume nitrogen;
10% by volume xenon/30% by volume oxygen/60% by volume nitrogen;
10% by volume xenon/25% by volume oxygen/65% by volume nitrogen;

Further preferred ratios can include the following mixtures of argon and xenon:
10% by volume xenon/40% by volume oxygen; 50% by volume argon
20% by volume xenon/50% by volume oxygen/30% by volume argon;
25% by volume xenon/50% by volume oxygen/25% by volume argon;
30% by volume xenon/30% by volume oxygen/40% by volume argon;
30% by volume xenon/40% by volume oxygen; 30% by volume argon
30% by volume xenon/50% by volume oxygen/20% by volume argon;
40% by volume xenon/30% by volume oxygen/30% by volume argon;
40% by volume xenon/50% by volume oxygen/10% by volume argon;
40% by volume xenon/35% by volume oxygen/25% by volume argon;
40% by volume xenon/40% by volume oxygen/20% by volume argon;
45% by volume xenon/50% by volume oxygen/5% by volume argon;
45% by volume xenon/45% by volume oxygen/10% by volume argon;
45% by volume xenon/40% by volume oxygen/15% by volume argon;
45% by volume xenon/35% by volume oxygen/20% by volume argon;
45% by volume xenon/30% by volume oxygen/25% by volume argon;
50% by volume xenon/45% by volume oxygen/5% by volume argon;
50% by volume xenon/40% by volume oxygen/10% by volume argon;
50% by volume xenon/30% by volume oxygen/20% by volume argon;
55% by volume xenon/30% by volume oxygen/15% by volume argon;
55% by volume xenon/35% by volume oxygen/10% by volume argon;
55% by volume xenon/40% by volume oxygen/5% by volume argon;

Nitrous Oxide Mixtures

Preferred nitrous oxide gas mixtures provided herein have between 40-60% of the total gas volume in the cartridge as nitrous oxide. It is likewise preferred that the remainder of the volume is made up of a mixture of nitrogen and oxygen, or just oxygen. More specific embodiments include 45-55% nitrous oxide and 55-45% of oxygen or oxygen and nitrogen, and more specifically about 50% nitrous oxide and 50% oxygen.

Doses

The teachings herein are configured to deliver a precise dose to the user, without concern of over inhaling to the point of asphyxiation or other detrimental consequences. More specifically, the combination of the volume/pressure/ratio of gas mixture within the cartridge 4, the demand regulator 6, and the instructions on breath type helps to ensure the medical objectives are achieved by the user. Multiple safety checks can be used to prevent over inhalation of asphyxiant gases and non-exclusively include: limiting the ratio and volume of said gases in the cartridge, limiting the size of the cartridge, adjusting the pressure within the cartridge. For example, if a dose is prescribed as 10 L of gas mixture, the cartridge can be a 10 L cartridge to hold 1 dose or 20-40 L, to hold 2 or 4 doses, for example. An upper limit of cartridge volume can be used to prevent overdosing and to stay below any toxicity limits of the gases described herein.

The volume of gas delivered can be changed by changing the size and or pressure of the cartridge 4. It is preferred to provide a cartridge 4 that could deliver between 1-10 doses of a gas mixture. Preferred doses include between 6-14 L, and more preferably around 10 L. Preferred cartridges hold about 10-70 L of gas mixture.

The delivery of a dose can constitute a single inhalation, but more preferably includes 2 or more inhalations depending on the contents of the cartridge 4. Dosages constituting 2 or more inhalations can be dispensed and/or monitored in a multitude of ways: by simply counting number of inhalations, and monitoring the pressure gauge 16 or counter on the regulator 6. According to certain embodiments, the devices herein can include automatic lockout devices after a certain volume of gas has been inhaled. Lockouts can be any configuration that blocks the patient from inhaling, such as blocking a passage in an inhalation device. In other examples, a medical provider can direct the lockout through a network after a certain volume of gas has been inhaled.

As an example for dosing, a 30 L cartridge can hold 3 doses of 10 L, a patient would breathe as instructed by his medical provider to obtain 10 L (e.g., breathing a certain way, a certain number of times, or until the pressure gauge reaches a certain value, or until symptoms reside). As a rough estimate a person average inhalation can be about 0.5 L, and so to obtain a 10 L dose, they would be breath normally 20 times. The volume of a patient's inhalation can be measured by a medical provider prior to receiving breath type instructions. As patient's experiencing stress may have difficulty controlling their breath type, instructions can be based on a number of breaths, or breathing until a certain volume, pressure, or number of breaths is reached.

Conditions Treated

The devices and methods of treatments herein can be used to treat, prevent, or alleviate any health condition that a noble gas mixture or nitrous oxide has efficacy in. According to preferred embodiments, the devices and methods herein can be used by people suffering from a variety of ailments such as neurological conditions, stress, anxiety, depression, including PTSD, Panic attacks, and Alzheimer's, inflammatory and pain disorders or have recently suffered a brain trauma. Alternatively, the devices and methods herein can be used for the reduction in inflammation, pain relief, stimulation of regeneration, radioprotection, or chemoprotection.

Pressures/Gauges

According to preferred embodiments, the regulator 6 contains a dial gauge 16 to measure and indicate gas pressure which is in communication with the cartridge 4. The dial gauge 16 can be a mechanical gauge or electronic, and can be configured to provide a constant direct reading of the level of compressed gas mixtures within the cartridge 4. The pressure gauge can help indicate to the user how much gas mixture is remaining in the cartridge 4.

Alternatively, a mechanical or electronic counter can be coupled to the devices 2 herein to record the number of times the device 2 has been utilized (how many doses have been administered), and thus the user or a medical provider can determine how much gas is remaining in the cartridge 4 or a medical provider can determine total amount used from 1 or more cartridges 4.

Alternatively, the pressure gauge or counting device can be in operable contact with a network (e.g., internet), the network allowing a health care provider to quantify the number of times the device 2 has been used or how much pressure and/or volume remains in the cartridge 4. The device can include electronic counters and gauges and configured to communicate (e.g., BLUETOOTH®, wireless, USB cord) with a computer and/or network to transfer these measurements. These measurements can be stored or analyzed by the user and/or medical provider, for example.

Breath Type and Instructions

As used herein the term "breath type" refers to the characterization of the user's particular inhalation(s)/exhalation(s) through the regulator. As described herein, the amount of gas delivered from the cartridge into the regulator, and ultimately into the patient's lungs, is dependent upon the particular "breath type" the patient performs. For example, if a patient breathes a shallow, short breath he/she will not inhale as much gas as with a deep, long breath. "Breath type" can thus refer to one or more of the following non-exclusive variables: length of inhalation or exhalation, length of time holding the inhalation, total number of individual inhalations/exhalations, strength or depth of inhalation or exhalation, and whether the breathing is diaphragmatic, thoracic, or clavicular based. Accordingly, instructions for a "breath type" that accompany the disclosed devices and methods could be 3 to 5 slow, deep inhalations for 5 seconds, holding for 5, and exhaling for 5 seconds. Another example of a breath type instruction could be to have the patient breathe deeply and slowly until the contents of the cartridge are exhausted or are locked out. Still another breath type instruction could be to breath normally until the pressure gauge on the regulator reaches a certain value that is lower than a starting value.

As the gas mixtures disclosed herein have inherent danger of being known asphyxiants, the medical instructions accompanying the disclosed devices and methods are important for the patient's safety and the efficacy of their treatment. If a medical provider prescribes a certain amount of gas to the patient, these accompanying instructions on breath type will allow the patient to safely and effectively utilize the devices and methods herein to meet the goals set by their medical provider.

Instructions on breath type can be in any suitable format including verbal or written (including words and/or graphics such as physical and digitally written instructions). Thus, a patient's use of the device only requires their recall memory or a quick examination of the provided written and/or graphical Instructions For Use (IFU) for proper operation. According to preferred embodiments, the breath type instructions herein will be written and accompany the portable gas delivery devices described herein. Additionally, it is preferable that the instructions include maximal amounts of gas to be inhaled for a given period of time (e.g., no more than 5 L per day). Instructions can also give further recommendations and proscriptions for gas use, including whether to use with or without food or water, contraindications with other drugs, and other safety warnings (e.g., not operating vehicles or heavy machinery after use).

The invention claimed is:

1. A portable, handheld, gas delivery system, said gas delivery comprising:
   i) a sealed pressurized cartridge containing a predetermined amount of compressed therapeutic gas mixture comprising either nitrous oxide or a noble gas mixture and having a topside and underside;
   ii) a demand regulator comprising:
      (a) a cartridge receiver configured to releasably couple with the topside of the pressurized cartridge in a sealed connection with the regulator and allow intake of the gas mixture into the regulator based on the inhalation type of the patient;
      (b) an inhalation device; and
      (c) an outtake,
      where said demand regulator is configured such that the inhalation of the patient through the inhalation device actuates the release of a portion of the gas mixture from the pressurized cartridge through the cartridge receiver into the regulator while lowering the pressure of the gas mixture within the regulator to ambient pressure, and then allows the gas mixture to enter into the patient's lungs from the regulator through the inhalation device; and further allows the patient's exhalation through the inhalation device to be released from the regulator through the outtake;
   iii) instructions from a medical provider to the patient directing a breath type during use; and
   iv) a cage coupled to the regulator configured to house the cartridge when coupled to the cartridge receiver and further comprising a cam and lever operably coupled to the cage at a pivot point that allows the cam and lever to swivel into open and closed positions, such that the cam can swivel to engage with the underside of the cartridge to apply pressure to the cartridge towards the cartridge receiver and swivel in the opposite direction to release the cartridge.

2. The gas delivery system of claim 1, wherein the sealed pressurized cartridge comprises a valve that is closed in its natural position and configured to open and allow the gas mixture to enter the regulator when operably coupled with the cartridge receiver.

3. The gas delivery system of claim 2, wherein the cartridge comprises a spring loaded check valve and the cartridge receiver comprises a regulator stem configured engage with the check valve pushing it away to open and allow gas to escape release from the cartridge when the cartridge is operably coupled with the cartridge receiver.

4. The gas delivery system of claim 1, wherein the sealed pressurized cartridge comprises two or more doses of the therapeutic gas mixture and the gas delivery system comprises either a pressure gauge and/or breath counter to indicate to the medical provider and/or patient how many doses of therapeutic gas mixture remain within the sealed pressurized cartridge.

5. The gas delivery system of claim 1, wherein the sealed pressurized cartridge is not operably coupled with the cartridge receiver through the use of complementary threads.

6. The gas delivery system of claim 1, wherein the gas delivery system is configured to automatically lock and thus prevent inhalation of gas after a predetermined number of breaths or cartridge pressure level have been reached.

* * * * *